United States Patent [19]

Builder et al.

[11] Patent Number: 4,620,948

[45] Date of Patent: Nov. 4, 1986

[54] PURIFICATION AND ACTIVITY ASSURANCE OF PRECIPITATED HETEROLOGOUS PROTEINS

[75] Inventors: Stuart E. Builder, Belmont; John R. Ogez, San Mateo, both of Calif.

[73] Assignee: Genentech, Inc., South San Francisco, Calif.

[21] Appl. No.: 615,681

[22] Filed: Jun. 1, 1984

Related U.S. Application Data

[63] Continuation of Ser. No. 452,344, Dec. 22, 1984.

[51] Int. Cl.[4] .......... C08G 3/12

[52] U.S. Cl. .......... 530/419; 435/68; 435/70; 435/240; 436/548

[58] Field of Search .......... 260/112 R; 424/85; 435/68, 70, 172, 240, 241, 948; 436/548

[56] References Cited

U.S. PATENT DOCUMENTS

| | | | |
|---|---|---|---|
| 4,414,150 | 11/1983 | Goeddel | 260/112 R X |
| 4,438,032 | 3/1984 | Golde et al. | 260/112 R |
| 4,462,940 | 7/1984 | Hanisch et al. | 260/112 R |

FOREIGN PATENT DOCUMENTS

| | | |
|---|---|---|
| 48970 | 4/1982 | European Pat. Off. . |
| 68693 | 1/1983 | European Pat. Off. . |
| 68691 | 1/1983 | European Pat. Off. . |
| 75444 | 3/1983 | European Pat. Off. . |
| 77670 | 4/1983 | Euorpean Pat. Off. . |
| 89233 | 9/1983 | European Pat. Off. . |
| 122080 | 10/1984 | European Pat. Off. . |
| WO8304418 | 12/1983 | PCT Int'l Appl. . |

OTHER PUBLICATIONS

Williams et al., Science 215, 687-688 (1982).

Goeddel et al., Proc. Natl. Acad. Sci. USA 76, 106-110 (1979).

Wetzel et al., Biochemistry 19, 6096-6104 (1980).

Wetzel et al., Gene 16, 63-71 (1981).

Ullmann et al., Biochem. Biophys. Res. Commun. 35, 35-42 (1969).

Goeddel et al., Nature, vol. 281, pp. 544 to 548 (Oct. 18, 1979).

Kleid et al., Science, vol. 214, pp. 1125 to 1129 (Dec. 4, 1981).

*Primary Examiner*—Howard E. Schain

[57] ABSTRACT

A process for isolating and purifying refractile proteins from host cell culture including treating the host cell culture with a buffered solution to solubilize host protein, leaving refractile protein insoluble, treating the insoluble fraction with a strongly denaturing solution containing a reducing agent to solubilize the refractile protein, and renaturing the refractile protein.

16 Claims, 9 Drawing Figures

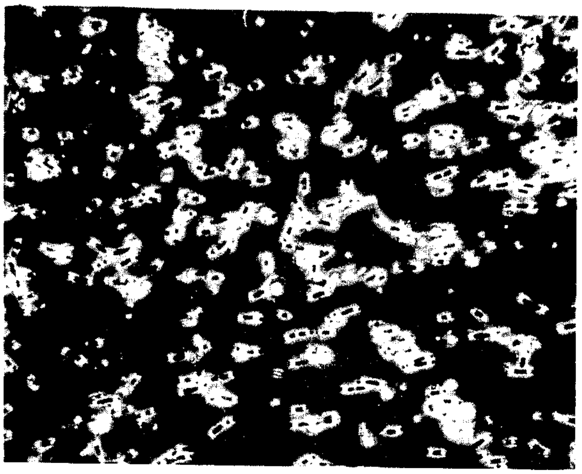
Fig.1. Phase contrast photomicrograph of cells expressing a long-fusion 33K urokinase. (E.coli K12 (W3110/pUK 33 trp $LE_L$)).
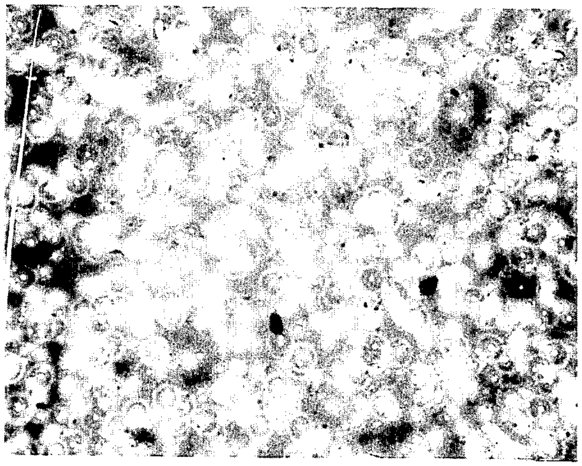
Fig.2. Phase contrast photomicrograph of pellet resulting from cell of figure 1 when subjected to the procedure of Example 1.

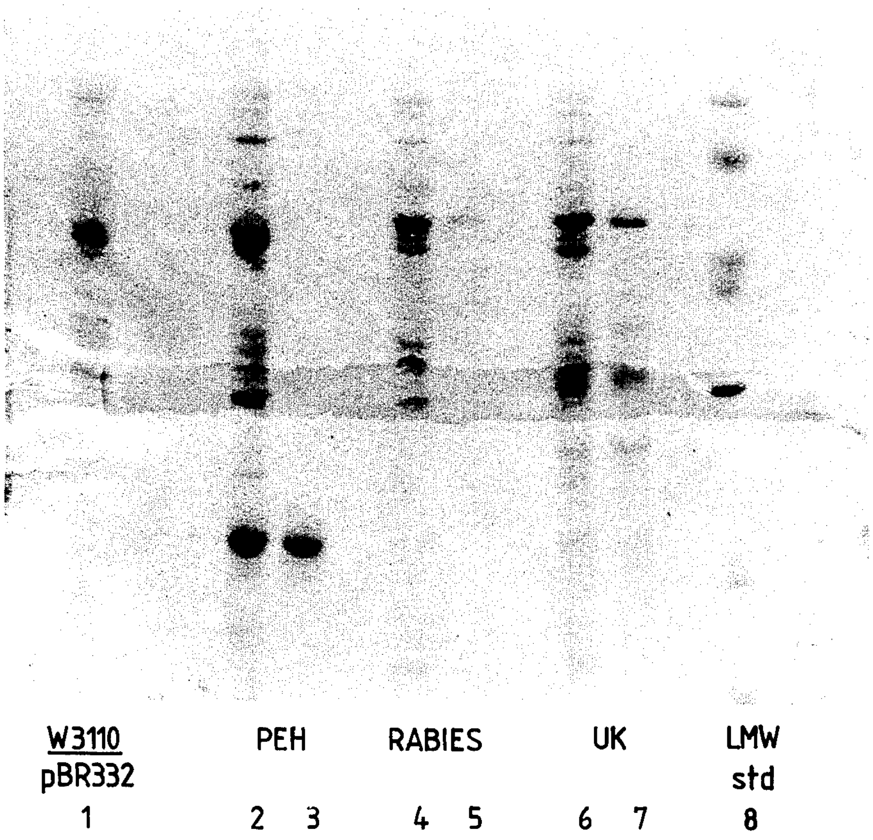

Fig.3. SDS PAGE of sonicates from whole cells (lanes 2, 4, 6) and from pellets as prepared according to Example 1 (lanes 3, 5, 7) from the cell cultures producing refractile bodies for respectively pGH, rabies antigen and urokinase (UK). While the whole cell shows a mixture, the pellets contain substantially only desired protein. Lane 1 is a sonicate from E.coli K12 W3110 transformed with the "blank" plasmid pBR322.

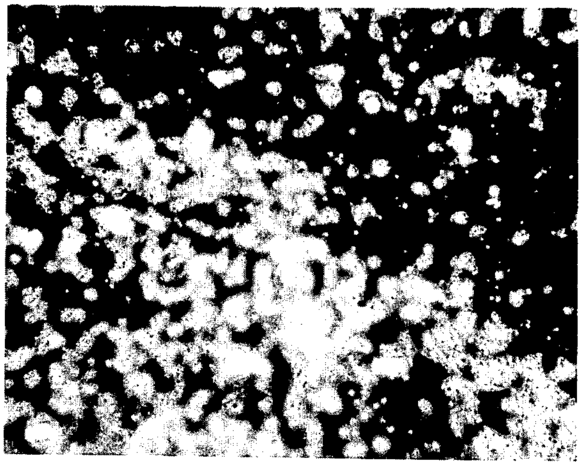
Fig.4A. Photograph through a phase contrast microscope of suspended pelleted refractile bodies from E. coli K12(W3110/p107), recovered as described in Example 2.
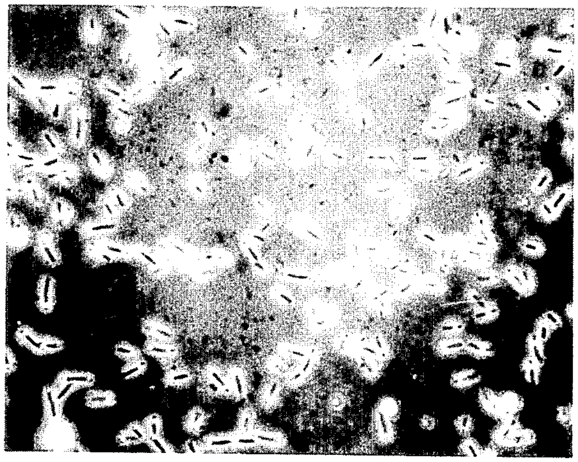
Fig.5A. Suspension of cell paste from E.coli K12(W3110/pGH-ex 1).

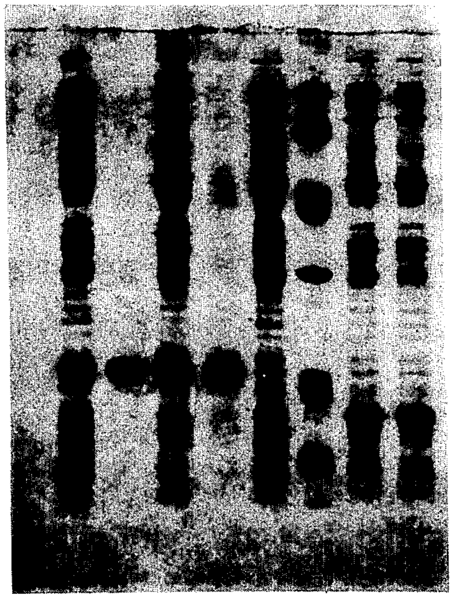

1 2 3 4

*Fig.4B.* SDS PAGE of killed and non-killed samples of cells corresponding to those in Figure 4A.

Lanes 1 and 3 are whole cell lysates from killed and non-killed cells respectively. They show protein mixtures and approximately equal amounts of hGH.

Lanes 2 and 4 are extracts from refractile bodies (pelleted) from killed and non-killed cells respectively. The killed cells show enhancement of the hGH band.

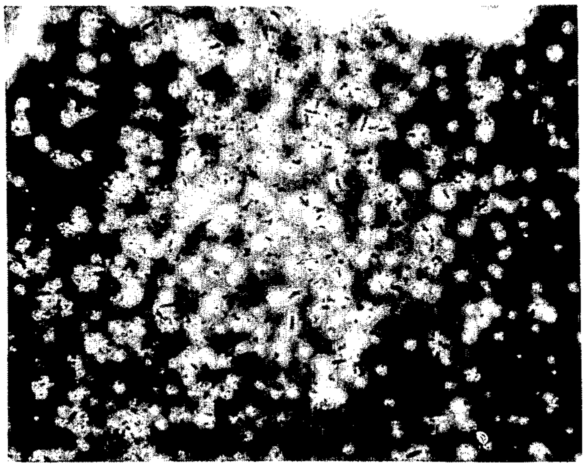
Fig.5B. Sonicate of paste of Figure 5A.
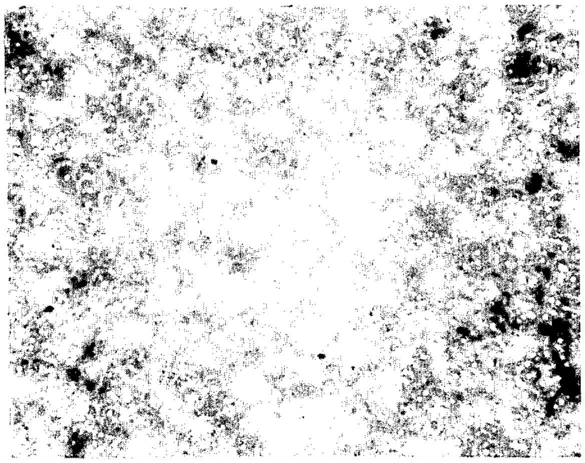
Fig.5C. Pellet of sonicate of Figure 5B.

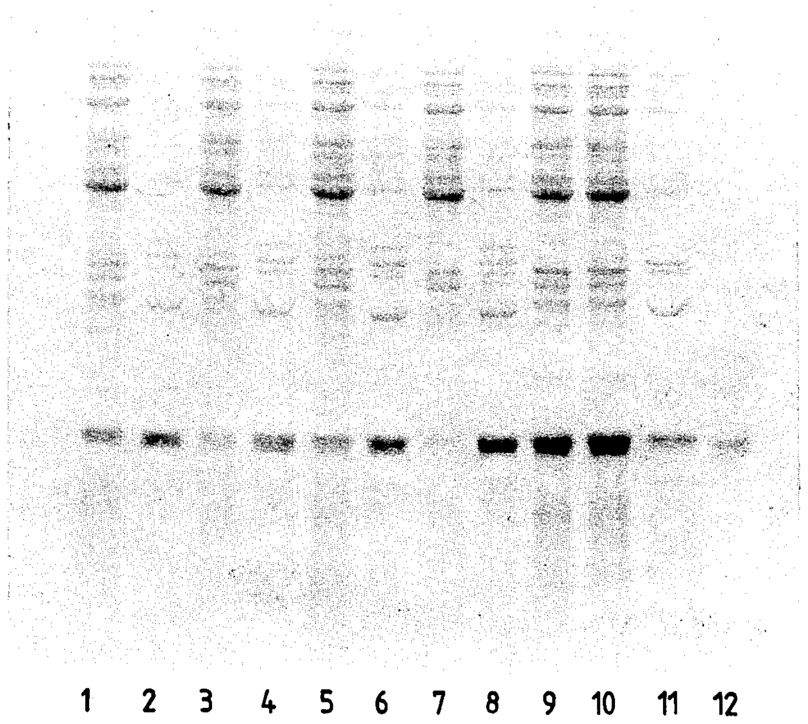

Fig.6. SDS PAGE of killed (PT) and non-killed (NPT) hGH-expressing E.coli K12(W3110/p107).

Lane 12 is a pure sample of hGH.

Lanes 9 and 10 represent SDS extracts of whole NPT and PT cells, respectively. Each gives a mixture of protein, with a strong band corresponding to hGH.

Lanes 1 and 5 show the supernatant from LSS and HSS of NPT cells; lanes 3 and 7 show the supernatant from LSS and HSS of PT cells. The intensity of the hGH band in lanes 3 and 7 (PT) is greatly reduced.

Lanes 2 and 6 represent pellet from LSS and HSS of NPT cells; lanes 4 and 8 the pellets of PT cells. The hGH band appears enhanced for the PT cells.

PURIFICATION AND ACTIVITY ASSURANCE OF PRECIPITATED HETEROLOGOUS PROTEINS

This application is a continuation of application Ser. No. 452,344, filed Dec. 22, 1984.

BACKGROUND OF THE INVENTION

Recombinant DNA technology has permitted the expression of exogenous or foreign (heterologous) proteins in bacteria and other host cells. Under some conditions, and for some proteins, these heterologous proteins are precipitated within the cell as "refractile" bodies. The present application concerns procedures for recovering these heterologous proteins and for restoring them, if necessary, to their active forms.

A large number of human, mammalian, and other proteins, including, for example, human growth hormone, (hGH) bovine growth hormone (bGH) and a number of interferons have been produced in host cells by transfecting such cells with DNA encoding these proteins and growing resulting cells under conditions favorable to the expression of the new heterologous protein. Viral coat proteins, such as capsid proteins of foot and mouth disease (FMD) virus and the surface antigenic protein of hepatitis B virus (HBsAg) are still other examples of heterologous proteins which have also been produced in suitable recombinant DNA engineered hosts. The heterologous protein is frequently precipitated inside the cell, and constitutes a significant portion of the total cell protein.

In a large number of important cases, such as those of hGH, porcine growth hormone (pGH), bGH, FMD, and fibroblast interferon (FIF), it has been observed that the heterologous proteins produced are not only present in large quantity, but are precipitated within the cell in the form of "refractile" bodies. The term "refractile" is used because these bodies can actually be seen using a phase contrast microscope. Under magnifications as low as 1000 fold, these precipitated protein bodies appear as bright spots visible within the enclosure of the cell.

Recovery of the desired protein which is in the form of such refractile bodies has presented a number of problems. First there is the obvious need to separate the refractile protein, which is encased within the cell, from the cellular material and proteins harboring it. Second, it appears that while the refractile body may often consist of a large percentage of the desired heterologous protein, and only a small portion of undesired ones, in some instances there are sufficient protein contaminants that these must be removed to isolate desired polypeptide sequence. Third, and perhaps most troublesome, the refractile body protein is often in a form which, while identifiable as the desired protein, is not biologically active. It is believed that this inactivity is due to incorrect folding or conformation of the heterologous protein either before or after intracellular precipitation, or during the isolation process.

It has now been found that these problems can be overcome by utilizing procedures which, in their various aspects, succeed in removing the contaminating host cellular protein, solubilizing the precipitated refractile protein, and restoring the heterologous protein to a form which is active in biological assays.

SUMMARY OF THE INVENTION

This application is directed to various aspects of an invention which provides an overall solution to what has emerged as a generalized problem: recovering, in active form, proteins which have been produced in host cells, which are heterologous thereto, and which are at least partially deposited inside the cells as refractile bodies i.e. clumps of insoluble protein. This approach, which provides an effective protocol for recovery of heterologous proteins from cell cultures wherein refractile bodies are formed, is presented in diagramatic form, including the various available alternatives, hereinbelow as Scheme 1.

Briefly described, scheme 1 has several phases: First, the precipitated insoluble protein is liberated from the cells by employing means which disrupt the outer cell wall/membrane under conditions comprising sufficient ionic strength and proper pH so that the host cell proteins, provided the cells are sufficiently disrupted, will be solubilized, or at least will fail to be brought down by low speed centrifugation. Accordingly, upon centrifugation the desired refractile protein will be accumulated in the pellet, and most of the contaminating proteins will then remain in the supernatant. The pellet, however, may contain contaminating proteins for several reasons. First, the original refractile body may not have been entirely comprised of the desired protein. Second, fragments of cell walls or membranes may be insufficiently disrupted so that they remain with the pellet and are undetected even upon microscopic examination of the pellet. However, the pellet which results will be predominantly the desired protein, and, unlike the situation found in standard protein purification procedures used in enzymological studies, the problem becomes one of removing contaminants from a basically pure product, rather than isolating a small component of a complex mixture.

(In some instances, notably that of human growth hormone, the heterologous protein produced by the bacterium or other host organism is only partially in refractile form as the cells are grown and the gene for the protein expressed. In those instances, it has been found that enhancement of the quantity of the desired protein contained in the pellet can be obtained by treating the cells, prior to disruption, with methods which were traditionally designed to kill the cells in compliance with safety precautions related to recombinant DNA transformed cells. Such techniques as acid, heat, or treatment with nonpolar solvents, appear to complete insolubilization of partially soluble proteins.)

Having secured a preparation which, is predominantly the desired protein, the problem now remains that the protein must be further purified in some instances, and recovered in a form wherein its biological activity can be utilized.

Since the protein has been precipitated in vivo under cytoplasmic conditions, it is clear that conventional solubilization techniques will fail. Accordingly, a more drastic means is required to bring this protein into solution so that it can be used. It has been found that a strong denaturing solution is effective in doing this. However, the resulting solution may or may not provide a biologically active preparation.

In addressing the problem of utilizing this solution which contains both strong denaturant and solubilized refractile protein to recover biological activity as shown by appropriate assays, the most "obvious" alternatives fail to yield successful results: Dilution, if necessary, with larger amounts of the same "solvent"—i.e. more of the strong denaturing solution, to obtain the proper concentration for biological testing is clearly undesirable because the strong denaturant itself would interfere with biological activity. Dilution of the solution with dilute buffer or with water is also unworkable in that reprecipitation of the refractile protein almost invariably occurs; even if dilution does not result in precipitation, the expected levels of activity are often not shown.

There are a limited number of successful alternatives for recovering biologically active product which are consistent with the general scheme of purification herein described. One of these is replacing the strong denaturant with a weaker one, followed by reduction of the concentration of the weak denaturant. This procedure appears to preserve the solubility of the refractile protein, and provide a medium which itself does not interfere with the biological activity. While it has been found that in some cases, this procedure alone does not result in positive biological activity, in other cases it does. The fusion protein formed which includes a foot and mouth disease (FMD) viral coat protein is one such instance. This also seems to be the case with respect to animal growth hormones. Where these circumstances occur, it is sufficient to dissolve the pellet in the strong denaturant, buffer exchange into a weak denaturant, or weaken the chaotropism by limited dilution, further purify it, if desired, using conventional techniques, and finally to buffer exchange gradually into more dilute solution.

However, according to presently known data, success of this scheme in recovering biologically active protein seems to be the exception rather than the rule. In many instances, apparently, more positive steps need to be taken to "renature" the protein which has been dissolved. The denaturation which has taken place may be the result either of original misfolding in the bacterium or of the isolation conditions or both. In any case, it appears prudent to unfold and refold the resulting protein using one of the three following approaches, all of which require buffer exchange into weak denaturant (which is, alone, sufficient in some cases) prior to reformation of disulfide bonds. In one approach, the protein is simply further purified under reducing conditions which guarantee the conversion of any disulfide linkages to sulfhydryl groups, to permit it to refold itself under the conditions of purification, and then to allow air or some other oxidizing agent to reform the disulfide bonds when the proteins have been properly refolded. A second approach is to break any disulfide linkages which may have been formed incorrectly, by sulfonating the protein, again allowing the protein to refold under more amenable conditions, and then reforming the disulfide bonds by removal of the sulfonate using a sulfydryl reagent in both its reduced and oxidized (disulfide) form. A third alternative is to allow the refolding to occur in the presence simply of the proper solution environment and in the presence of a sulfhydryl-disulfide combination so that sulfhydryl and disulfides are constantly being formed and reformed.

In any event, this "renaturation process" appears best to take place concommitant with further steps for purification of the protein i.e. ridding it of the minor contaminants that it contains after simple dissolution from the pellet.

This application, then, is directed to an invention which in its various aspects, provides a successful protocol for heterologous protein preparation.

In one aspect, the invention concerns a process for isolating the refractile protein from background host cell protein through lysis of a suspension of host cells followed by recovery of the refractile bodies through centrifugation at low speed. The course of this purification process can conveniently be followed by examination of the preparation under a microscope to determine the presence or absence of fragments of bacterial cell walls, fragments or whole cells.

In another aspect, the invention concerns a process for enhancing the amount of heterologous protein which is precipitated in refractile form prior to isolation of the refractile bodies. The process involves treating a suspension of the host cell culture with a killing protocol, such as high acid concentration, heat, or low concentrations of nonpolar organic solvents. This "kill" treatment results in further precipitation of heterologous protein, and is then followed by the procedures disclosed in other aspects of the invention to recover the increased amounts of precipitated protein.

In a third aspect, the invention concerns a process for recovering the refractile protein in a usable form by solubilizing it in a strongly denaturing solution. This process may contain the additional step of treating a suspension of the host cells in a buffer of suitable ionic strength to solubilize the host cell protein, before recovery of the desired refractile protein.

In a fourth aspect, the invention concerns a process for further purification of the refractile protein previously solubilized in a strongly denaturing solution, preferably in the presence of a reducing agent, which comprises separation away of large molecular weight contaminants using either a molecular sieve or high speed centrifugation.

In still another aspect, the invention concerns steps to utilize or further purify the heterologous protein already dissolved in strongly denaturing solution, wherein the solution is modified by weakening the denaturing medium by dilution or by exchange with a weak denaturant, optionally in the presence of reducing agent. Under the influence of weakly denaturing conditions, in some instances, aided by the reducing agent available,, refolding is permitted to take place. The weak denaturant replacement is also advantageous because it permits further purification and/or renaturation steps to be conducted which would fail in strongly denaturing surroundings.

Such replacement can conveniently be done by buffer exchange against a comparable concentration of a denaturant whose chaotropic properties are inherently weaker (such as, for example, replacing guanidine with urea) or by dilution (if the solubility characteristics of the subject protein will permit) to a decreased concentration of the same strong denaturant.

Still another aspect of the invention concerns a specific reactivating process which is carried out in the presence of a weakly denaturing medium. In this process, the refractile protein, which is solubilized in a strongly denaturing solution, is treated with a mild oxidizing agent in the presence of sulfite ion. This converts cysteine and cystine containing proteins to the protein-S-sulfonates. The strongly denaturing solution is then weakened to permit refolding, and disulfide linkages are reformed using a sulfhydryl compound such as, for example, β-mercaptoethanol or reduced glutathione, in the presence of the corresponding disulfide (oxidized) form.

In another aspect, the protein solubilized in strong denaturant is further processed by refolding which comprises replacement of the strong denaturant with a weak one and treating with a mixture of a sulfhydryl compound, predominantly, along with its disulfide form in lesser amount, i.e. a one-step refolding procedure in "redox buffer".

In still another aspect the invention is directed to purification procedures carried out in the presence of a reducing agent such as, for example, β-mercaptoethanol followed by the denaturant and reducing agent being removed by dialysis or other suitable means. If no pains are taken to exclude air, this then serves to reoxidize the protein to reform disulfide linkages, formation of which had been thwarted by the presence of reducing agent.

The invention also relates to a "standard" multistep process for purification of heterologous proteins precipitated in host cell cultures which comprises the steps of removing the soluble background host proteins in a solution of proper salt concentration and pH, followed by solubilizing the heterologous precipitated protein in a denaturing solution containing a reducing agent, and recovering from the denaturing solution the desired protein in renatured form. Additional steps to achieve further purification of the desired protein are optional and may be selected from a number of conventional techniques but are carried out in the presence of reducing agent. These steps preferably comprise, for example, size separation by gel permeation chromatography, and removal of undesired proteins by differential adsorption on an ion exchange resin.

This aspect of the invention provides a general procedure which is applicable to precipitated heterologous proteins in host cell culture, regardless of their biological nature and thus has the advantage of offering uniformity of equipment requirements for any desired product. This procedure is applicable generally with only minor modification or adjustments being required for specific proteins.

Finally, the various aspects of this invention by suitable combination and selection thereof, provide a solution to the problem of refractile body protein.

BRIEF DESCRIPTION OF THE DRAWINGS

FIG. 1 shows the cell paste, under a phase contrast microscope, of *E. coli* cells expressing a fusion protein containing urokinase (UK).

FIG. 2 shows a suspension of pellet resulting from low speed centrifugation of the disrupted cells from FIG. 1 (again, as seen through a phase contrast microscope).

FIG. 3 shows the results of SDS PAGE on preparations of pGH, rabies antigen, and urokinase, contrasting the content of impurities to the desired protein in the crude sonicate of cells with that of isolated refractile bodies prepared according to the method of the invention.

FIG. 4A is a photograph of the partially isolated refractile bodies of human growth hormone isolated from *E. coli.*

FIG. 4B is a photograph of an SDS PAGE gel contrasting the whole cell lysate with the refractile body protein content for both live and killed cells.

FIG. 5A is a photograph of *E. coli* whole cells containing refractile bodies of pGH.

FIG. 5B is a photograph of the sonicate of the preparation in 5A.

FIG. 5C is a photograph of the centrifugation pellet when the sonicated suspension of B is centrifuged at low speed.

FIG. 6 shows the results of SDS PAGE on supernatant and pellet fractions of killed and nonkilled cells.

DETAILED DESCRIPTION OF THE INVENTION (A) Definitions:

"Heterologous" proteins are proteins which are normally either not produced at all by the host cell, or normally are produced only in limited amounts. The advent of recombinant DNA technology and other standard genetic manipulation such as point mutagenesis, has enabled the production of heterologous proteins in copious amounts from transfected host cell cultures. In practice, these heterologous proteins are frequently produced by genetic expression in quantities that involve their precipitation under conditions which maintain the solubility of host cellular proteins.

In some instances, the insolubility of the expressed protein is such that these proteins are present in the host cell as so-called "refractile bodies," i.e., bodies which refract light and appear as bright spots when viewed through a phase contrast microscope. Hence, the proteins are often referred to as "refractile proteins" or "refractile body proteins".

The invention herein is directed to procedures which are useful in isolating, purifying, and, if necessary, reactivating proteins which appear in host cells in the form of "refractile bodies". Part of the invention concerns methods which encourage such refractile body formation; however, the procedures for protein recovery and activation disclosed herein are intended to be specifically applicable to such refractile proteins.

In the herein specification "refractile", "desired" and "heterologous" are used interchangeably to denote a protein expressed in a foreign host which is, at some stage of expression or purification, visible by phase contrast microscope as a precipitate, regardless of the physical state of the protein at the time it is referenced. E.g. "refractile" protein will still be used in some instances to denote said protein even after it has been converted from refractile to soluble form by the process of the invention.

Various heterologous proteins expressed in bacterial host cells, for example, pGH, hGH, and viral coat proteins such as a fusion protein with FMD virus, protein and HBsAg form refractile bodies to a greater or lesser extent under commonly found culture conditions. Certain other proteins such as immune interferon (IIF) and leukocyte interferon (LeIF) are more soluble in the cytoplasm. (Fibroblast interferon (FIF) is, however, refractile in host culture.)

"Host cells" includes, where used in the context of a starting material in a procedure description for heterologous protein isolation, any of the forms in which the cells could be so used. It includes, for example, besides the harvested cell paste, the entire cell culture, a frozen sample of the paste, or a frozen and thawed sample of the paste. Thus the phrase "treating host cells in a buffered solution" may refer, for example, to manipulation of the whole culture broth or to a preparation using spun down cells.

"Reactivation", as used herein, is almost synonymous with "refolding"—i.e., it refers to assurance of biological activity for a protein preparation by placing it in a conformationally active form. "Reactivation" does not, as defined herein involve any change in the amino acid sequence and does not include, for example "activation" of the type wherein peptide precursors are cleaved to their active forms, such as conversion of trypsinogen to trypsin or prorennin to rennin.

"Biological activity" will refer to the activity of the protein in vivo, to its activity in conventional in vitro and in vivo biological assays designed to test its functionality, to its ability to elicit an immune response, or to the ability of the protein to react with antibodies to the native protein. It is to be noted that in some cases, for example, proteins are "biologically active" when tested for reactivity with the appropriate antibodies, but not in functionality assays. However, as antibody reactivity is generally the most straightforward and easily performed assay method, it is sometimes used as a convenient measure of "activity".

"Ionic strength" refers to the conventional measure of ion concentration in aqueous solution. It is defined as ½ of the sum (over all ions in solution) of the product of the concentration of each ion, times the square of the charge thereon.

"Denaturing solution" refers to a solution which contains a "denaturant". "Denaturant", as used herein, refers to those chaotropic compounds or materials which, in aqueous solution and in suitable concentrations are capable of changing the spatial configuration or conformation of proteins through alterations at the surface thereof, either through altering, for example, the state of hydration, the solvent environment, or the solvent-surface interaction. Examples of such denaturants include urea, guanidine hydrochloride, sodium thiocyanate and detergents, such as SDS and Triton. It does not include such drastic and irreversible denaturing procedures as high temperature and high acidity.

It will be noted that some of the listed reagents are strong denaturants, while others are weaker, and that, of course, the concentration of any of these will directly affect its strength and effectiveness. There can be no specifically exact dividing line between "strong" and "weak", however, strong denaturing conditions more completely "unfold" the protein from whatever conformation it would spontaneously have preferred due to its amino acid sequence having conferred areas of hydrophilicity and hydrophobicity along the chain under physiological conditions. The most commonly used strongly denaturing environment useful in dissolving refractile protein is a fairly high (4–9M) concentration of the ionic denaturant, guanidine hydrochloride. Urea is the most frequently used example of a weak denaturant as even fairly high (e.g. 7M) concentrations permit the retention of some protein secondary structures, and provide a route to refolding to the "native" conformation. It happens also to be nonionic in character, which is significant with respect to its use in those aspects of the invention which entail the use of, for example, ion exchange techniques.

Accordingly, a "strongly denaturing" solution refers to a solution which will effectively "unfold" a protein also dissolved in the solution. The unfolding will be relatively extensive, but reversible. Solutes which are effective in carrying out unfolding to this extent are exemplified by guanidine hydrochloride and sodium thiocyanate, usually in relatively high concentrations in the range of approximately 4–9M, and detergents usually supplied in concentrations of the order of 0.01–2 percent.

"Weakly denaturing solutions" refers to those solutions which permit at least partial folding of a protein into the spatial conformation in which it finds itself when operating in its active form under endogenous or homologous physiological conditions, and also solubilizing any intermediate forms between the "denatured" form as would be found in a strongly denaturing solution, and the properly folded conformation. Examples of such weakly denaturing solutions are high concentrations of urea, ordinarily in the range of 4–9M and low concentrations of the denaturants set forth above which, in high concentrations, are strongly denaturing. These latter "low" concentrations are ordinarily in the range of 0.5 to approximately 2M. Occasionally, however, the functional status of "weakly denaturing solution" can also be observed simply under fairly standard enzyme assay conditions such as, for example, low buffer concentrations of the order of 0.1M and below, and physiological pH. As used in this invention, "weakly denaturing solution" refers to the functional definition—i.e. those solutions which permit refolding from whatever contorted conformation the protein has, for whatever reason, assumed through intermediates soluble in this solution, to a conformation which is capable of exhibiting biological activity.

There are abbreviations and descriptions conventionally used with regard to particular techniques that are used in this invention, and for convenience these will be described briefly here:

Gel permeation chromatography or gel filtration is a commonly used purification technique which discriminates between molecules according to their size. This is also frequently referred to as a "molecular sieve". By suitable selection of the gel, almost any size range can be selected for. Molecules which are large enough to be excluded from the gel pores are passed unretarded through a column containing the gel; smaller molecules are fractionated by the column.

SDS-PAGE (Sodium dodecyl sulfate-polyacrylamide gel electrophoresis) is a conventionally employed technique which permits determination of approximate molecular weight and purity. In this technique, the protein preparation is electrophoresed under reducing conditions in the presence of detergent. The extent of migration for a particular molecule is dependent only upon molecular weight as determined in the absence of disulfide linkages (due to the reducing conditions). Therefore, the quantity of a particular protein present in a preparation can be estimated by densitometry measurements on a stained band appearing at the position corresponding to the molecular weight of the protein. A detailed description of this technique is found in Laemmli, U.K., et al. *Nature,* 227: 680 (1970) incorporated herein by reference.

"Western Blot" refers to an antibody specific binding technique wherein a solution or suspension containing the protein to be measured is exposed to a nitrocellulose filter, which filter is then soaked with a labelled antiserum to the desired protein. The presence of the desired protein is ascertained by the retention of label on the filter due to the insolubilization of the antibody by reaction with the specific protein. A detailed description is provided by Towbin, H., et al., *Proc. Nat. Acad. Sci. (USA.)*, 76: 4350 (1979) incorporated herein by reference.

"Chromatographic ion exchange protein purification techniques" refers to a series of procedures wherein material is subjected to chromatographic separation based on an ionic exchange column interaction. Frequently used columns are, for example, DEAE cellulose, frequently denoted simply as DEAE or, for example, DE-52 or DE-53 as common trade names, or carboxymethyl cellulose (CMC). At appropriate pH values, a column containing DEAE behaves as an anion exchanger, and negatively charged particles bind to the column. Elution can be accomplished by from such columns altering the components of eluting solvents, for example, by altering the pH, the ionic strength, or dielectric constant of the solution, or even through regulation of temperature.

"Buffer exchange" refers to techniques whereby the effective "solvent" i.e., the liquid environment of a macromolecule is changed. Thus, in this sense, "solvent" really includes micromolecular solutes (e.g. salts) of the medium in which a desired macromolecule finds itself since, in fact, its solubility may be attributable to them. For example, in the process of a present invention, the desired protein may be prepared for ion exchange chromatography by providing a solvent comprising 8M urea in an appropriate buffer replacing, for example 7M guanidine hydrochloride, which, in one preferred embodiment, is used as a denaturant. To make this "buffer exchange", one suitable technique is dialysis of the 7M guanidine hydrochloride solution containing the protein against substantially larger quantities of the urea buffer. However, other buffer exchange techniques, such as, for example gel permeation and diafiltration are also available and workable.

B. General Description

Scheme 1 depicted below shows the general procedures involved in solving the problem of isolating an active desired protein from host cells wherein this protein has been produced and deposited in the form of refractile bodies.

Scheme 1

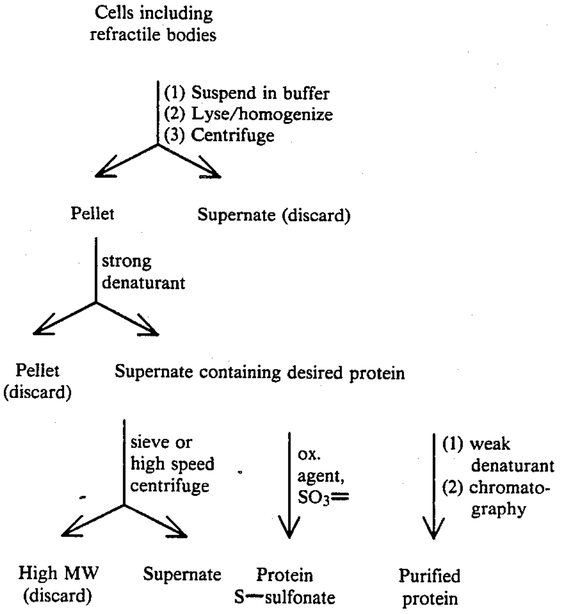

-continued

Scheme 1

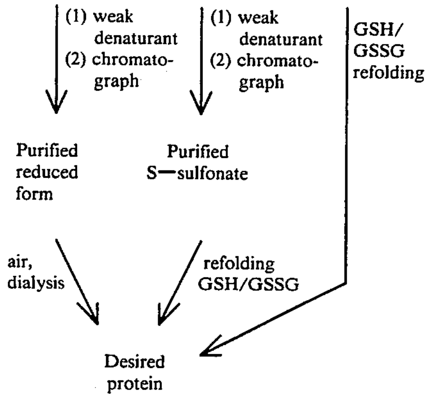

C. Recovery of Refractile Bodies

As shown in scheme 1, because the refractile bodies are enclosed in the cells, it is desirable first to disrupt the cells so as to release the refractile bodies and make them available for recovery by, for example, centrifugation. In one aspect of the invention, purification of refractile proteins is obtained simply by insuring that the cellular debris is sufficiently disrupted that it fails to appear in the pellet under low speed centrifugation. In this aspect of the invention, the cells are suspended in a buffer at pH 5 to 9, preferably about 6 to 8, using an ionic strength of the order of 0.01M to 2M preferably 0.1–0.2M. Any suitable salt, including NaCl can be used to maintain a proper ionic strength level. This ionic strength range is known to be adequate for the invention, although the exact outer limits of permissible ionic strengths are not clearly understood or known. It is, apparently, undesirable to use essentially zero ionic strength, however. The cells, while suspended in the foregoing buffer, are then lysed by techniques commonly employed such as, for example, mechanical methods such as use of a Manton-Gaulin press, a French press, or a sonic oscillator, or by chemical or enzymatic methods such as treatment with lysozyme.

When it is judged that the cells are sufficiently disrupted that there will be a minimum of, or no, cellular fragments of sufficient size to be spun down remaining, the suspension is centrifuged at low speed, around 500 to 5000 times gravity, preferably around 1000 times gravity in a standard centrifuge for a suitable time period depending on volume, usually about 10 minutes to ½ hour. The resulting pellet contains substantially all of the refractile proteins, but if the cell disruption process is not complete, it may also contain broken cell fragments. Completeness can be assayed by resuspending the pellet in a small amount of the same buffer solution, and examining the suspension with a phase contrast microscope. The presence of broken cell fragments indicates that further sonication or other means of disruption is necessary in order to remove the proteins associated with these fragments. After such further disruption, if required, the suspension is again centrifuged, and the pellet recovered, resuspended, and reexamined. This process is repeated until visual examination shows the absence of nonrefractile proteins in the pelleted material. With suitable preparations, the conditions for particular protein may be defined sufficiently clearly that in carrying out the process of the invention, only one such suspension, disruption, and centrifugation is required. However, even in this case it is preferable to carry out the process in the above several steps, most preferably a total of three as this permits a desirable reduction in required volumes of aqueous buffer (i.e. the amount used to resuspend the pellet is substantially smaller than the volume used in the original preparation), and the quality of the preparation is consistently assured by visual monitoring.

The proteins in the pellet so prepared contain from about 40 percent to over 90 percent of the desired heterologous protein as compared to total protein contained therein, depending on the specific protein produced by the host cell.

For example, when prepared by the particular procedures utilized in Examples 1 through 8, for human growth hormone more than 90 percent of the refractile protein was in fact the desired protein (as measured by the methods there indicated), while only about 50 percent was the desired protein in the cases of human interferons and of the viral antigenic proteins. Intermediate amounts were obtained of tissue plasminogen activator and calf rennin. These purities are, at this stage, adequate for some uses of the desired protein.

The pellet is capable of being dissolved in a solution of denaturant, which resulting solution as such may or may not contain an active form of the protein. The results of utilizing this method alone for isolating refractile proteins is exemplified in the aforementioned Examples 1 through 8 of the specification. It is most advantageously applied to heterologous proteins produced in bacterial culture, most preferably *E. coli* and for the isolation of proteins selected from the group consisting of hGH, bGH, pGH, human fibroblast interferon (FIF), human immume interferon (IIF), human tissue plasminogen activator (tPA), calf prorennin, and FMD coat proteins. The technique of dissolving the pelleted proteins in a denaturant and of recovering activity are borrowed from the other aspects of the invention, which aspects are set forth in the succeeding paragraphs.

D. Enhancing Production of Refractile Bodies

In a second aspect, the invention is related to a procedure for enhancing the quantity of protein, expressed in a foreign host cell which is insolubilized in refractile form, prior to purification thereof. In the case of many proteins, when growth and expression are obtained as set forth in the examples herein, enhancement is unnecessary because virtually all of the desired protein appears in the form of these refractile bodies, anyway. Exemplary of such proteins are animal growth hormones, and fibroblast interferon. However, in the case of human growth hormone, apparently only roughly 50 percent of the protein expressed by *E. coli* appears as refractile bodies, and a corresponding loss in yield will be experienced if these procedures are not followed. Similarly, immune interferon is largely produced in nonrefractile form, and if procedures directed to refractile bodies are to be employed for its isolation, enhancement must be effected by the methods set forth within this aspect of the invention.

In this procedure, advantage is taken of the desirability of utilizing a "kill" step whereby the recombinant cells can be brought into conformance with government regulations directed toward safety in the growth and harvest of such cells. A number of killing techniques are available, and have been carried out simply for safety purposes, but they have the additional desirable effect in the aforementioned instances of increasing the quantity of refractile protein. In the process of this aspect of the invention, the host cells may be killed either in the medium in which they are being cultured and grown, or in a suspension prepared by an initial centrifugation or other methods of concentration of the cells of the original medium, recovery of a cell paste, and resuspension in an aqueous solution. Suitable kill procedures are administration of low concentrations of acids, heat treatment, and, most preferably, treatment with nonpolar organic solvents in small percentage.

In a particularly preferred procedure, the culture medium is brought to 0.25 percent in phenol and 0.25 percent in toluene and allowed to incubate at room temperature to 45° C., preferably about 37° C. for 15 minutes to several hours most preferably 0.5 hours. Alternatively, if facilities are available for containment, the cells are first harvested under containment, resuspended in for example 0.1M–2M ionic strength, preferably 0.1–0.2M ionic strength buffer of pH 5–9, preferably 6–8. The suspension is then treated with low concentrations of organic solvents—e.g. 0.25 percent each in phenol and toluene.

In other embodiments, either the cell medium or suspension as above described can also be heated to about 60°–80° C. for about 15 min.–45 min. to effect killing; or brought e.g. to a pH of about 0.5–1.5.

These procedures result in considerable additional percipitation of the expressed heterologous protein, if it is not already so percipitated. Example 9 sets forth a particular instance in which this method is advantageous.

The procedure of this aspect of the invention can then be combined with further techniques, disclosed herein, for the recovery of active heterologous protein.

E. Solution of Heterologous Protein in Strongly Denaturing Solution

In a third aspect, the invention concerns a procedure for dissolving the refractile proteins from their insoluble or pelleted form by using a strong denaturing solution. While the proteins in refractile bodies are generally insoluble under the conditions prevailing in the cytoplasm (and thus in relatively weak ionic strength buffers) they appear to be soluble in fairly high concentrations, typically 4 to 9M concentrations, of certain denaturants. In the process of the invention, strong, often ionic, denaturants are apparently the most practical. A particularly preferred denaturant is a guanidine salt, although detergents such as Triton and SDS and salts of thiocyanate ion have also been used successfully. A range of 4 to 9M concentration is workable for guanidine salts or sodium thiocyanate, with 6–8M, being particularly preferred. Detergents are used in the range of 0.01–2 percent of solution. The pH of the solution must be compatible with the characteristics of the particular protein, so that irreversible denaturation or protein hydrolysis does not occur; optimum concentration of denaturant is dependent on the protein to be solubilized and the pH used.

While solubility, once achieved is often maintained when the solubilized heterologous protein is exchanged into a more weakly denaturing medium, initial solubilization in this same weakly denaturing medium is not practical. Whether for thermodynamic or kinetic reasons, the protein does not dissolve within a reasonable time under these less drastic conditions.

Additional components may be added to the solution to maintain the desired pH level, as may other ancillary components desirable in particular instances such as, for example, chelators such as EDTA. As shown by the behavior of the proteins in refractile bodies in Examples 1-8, 10, and 11, solutions which are not strongly denaturing typically fail do dissolve these refractile proteins (although host cellular proteins are dissolved), while strong denaturing solutions to dissolve them. Accordingly, such weakly denaturing buffers can also be used to solubilize and remove host cell proteins.

In the process of this aspect of the invention, the host cells are first suspended in a medium of correct ionic strength to solubilize many host cell proteins—i.e. 0.01-2M ionic strength, preferably about 0.4-0.6M ionic strength at a pH of about 5-9, preferably around 6-8. Precise pH and ionic strength limits cannot, or course, be set forth, but workable ranges are here given.

The cells are disrupted in the presence of the foregoing solution, and the suspension centrifuged to form a pellet. The pellet contains mainly the desired protein in refractile form, and it remains to employ the strongly denaturing medium described above to solubilize it. The solubilized protein may then be recovered using means which allow its renaturation.

F. Removal of High Molecular Weight Contaminants

In a fourth aspect, the invention is directed to a process for freeing the solubilized, desired, previously refractile protein from higher molecular weight components directly from the strongly denaturing solution, even if the denaturant is ionic, using either a molecular sieve or high speed centrifugation. The procedure follows the left-most series of arrows from the "supernatant containing desired protein" in Scheme 1, wherein the supernatant from the pellet which has been extracted with strong denaturant is either passed over a column of a size-discriminating gel permeation molecular sieve, such as sephacryl, or is centrifuged at high speed to bring down higher molecular weight components. Neither of these separation procedures requires removal of ions from solution, and hence can be carried out directly on the extract from the pellet, even if this extract is ionic. (See Examples 10 and 11.)

In carrying out the removal of high molecular weight impurities through gel filtration, a column containing a molecular sieve, such as, for example, Sephacryl S-300 is equilibrated in a suitable buffer (containing, preferably, a reducing agent) and the solution containing the heterologous protein passed through the column. The high molecular weight flow-through volume is descarded, and the heterologous protein then eluted with further amounts of buffer. Eluted protein may be monitored for example by measurement of optical density at 280 nm, and the presence of the desired protein verified by dialysis against a non-ionic solvent, followed by SDS-PAGE to ascertain the correct molecular weight protein.

In the alternative approach, high speed centrifugation is carried out by spinning the protein at 25,000-40,000×g, preferably 35,000×g for 10 min.-3 hrs, and recovering the supernatant for further purification.

Use of gel permeation chromatography as a first chromatographic step in a commercial purification process for protein, i.e. carrying out gel permiation prior to, for example, ion exchange chromatography, is unusual. However, in the process of the present invention the protein has a high level purity (virtually always as high as 50 percent or more) after just the lysis and/or denaturant extraction steps. Therefore, as compared to conventional procedures for the isolation of proteins, the desired protein is in a fairly high state of purity before it is subjected to the gel filtration step. Thus, the usual disadvantage—i.e., the lower capacity of gel filtration as compared to ion exchanges does not pertain in this case. Since the amount of impurities is small, a total high capacity is not needed as it would be to isolate a small amount of a particular protein from a large collection of impurities.

Further purification may optionally be carried out consistent with this aspect. If the dissolving denaturant was ionic, desalting the solution by exchanging into non-ionic denaturant is required if such further steps involve ion exchange. As a practical matter, it is preferable to utilize a weakly denaturing solution such as urea. While in principle the denaturant might simply have been removed by, for example, dialysis into standard types of buffer, this often results in reprecipitation of the protein. Maintaining the protein in a solution which still contains a reasonable denaturant concentration prevents premature precipitation of the protein. Once the ions have been removed and replaced by a non-ionic substance, a variety of chromatographic techniques involving ion exchange or neutral adsorption supports may be used for further purification. An advantageous choice among these is DEAE cellulose chromatography at such a pH that the desired protein fails to stick to the column and appears in the flow through volume. The column thus captures the anionic protein contaminants, and removes them from the desired protein. This approach, rather than the converse, wherein the desired protein is adsorbed and eluted, has the clear advantage of simplicity and of more limited resin requirements. Since the desired protein predominates in quantity, only sufficient resin to adsorb the contaminants is required. However, the process addressed by this aspect of the invention is not limited by any specific example, but rather permits the use of a variety of separation techniques as further purification methods.

G. Maintaining Solubility Without Strong Denaturant

Still another aspect of the present invention comprises the maintenance of solubility during purification by replacing the strongly denaturing solution of the subject protein with a weakly denaturing solution prior to subsequent purification or biological testing. In some cases, for example that of hGH expressed in *E. coli,* this alone may be sufficient to effect refolding, but this is not always the case. Further, in some instances and for some applications (e.g. where subsequent ion exchange is not involved) limited dilution of the strongly denaturing solution will suffice to maintain solubility for some proteins. However, a buffer exchange procedure whereby the strongly denaturing solution is replaced by a weaker one, is useful to maintain solubility while permitting further purification, and in some cases, restoration of biological activity. This is desirable, in particular, in the case of ionic strong denaturants, because, for example, it is often necessary to utilize ion exchange techniques in order further to purify partially purified refractile proteins. It is not possible to utilize the solution directly resulting from solubilization of refractile proteins because the ionic denaturant interferes with ion exchange. However, removal of this denaturant altogether often results in precipitation of the desired protein. These problems can be avoided by buffer exchanging an ionic strong denaturant such as guanidine, with a less powerful non-ionic one such as urea. In particular, urea appears, in reasonable concentrations—i.e. 1-9M approximately, both to permit refolding of the proteins into something approximating their native state whether supplied in the form extracted, or in S-sulfonated form as set forth in another aspect of this invention, and also (perhaps because of this) maintain solubilization.

The "buffer exchange" may be done in the presence of β-mercaptoethanol or another suitable reducing agent so as to maintain reduction of any improper disulfide linkage which might have been formed prior to the buffer exchange renaturing process or, alternatively, with the protein in the form of a S-sulfonate.

Accordingly, in the process of this aspect of the invention, the strongly denaturing solution containing the subject protein or its S-sulfonate and, for example, 4–9M guanidine HCl is buffer-exchanged using dialysis or diafiltration against a solution of urea or other weak denaturant which optionally contains a suitable concentration of reducing agent, before any subsequent purification takes place. (As set forth in another aspect of the invention, the original strongly denaturing solution may first treated with sulfite and a mild oxidizing agent in order to conduct sulfitolysis prior to buffer exchange against a weakly denaturing medium. This sulfitolysis procedure is not inconsistent with the scope of the present aspect of the invention.) in either event, the weakly denaturing solution contains protein which is folded more nearly to the form corresponding to the biologically active protein, (whether S-sulfonated or not) and the resulting solution can be subjected to the full panoply of purification techniques, such as ion exchange on an anion column such as DEAE cellulose or on a cation column such as CMC. In any case, the subsequent purification methods are conducted in a conventional manner at appropriate pH's and salt concentrations depending on the particular protein to be isolated, and on the specific strategy to be employed. Such subsequent purification methods are well known in the art and their application is familiar to the practitioners thereof.

H. Refolding

The remaining three aspects of the invention represent alternative procedures directed to reactivating an inactive (presumably because it is incorrectly folded) form of the desired protein.

In the first such aspect, refractile proteins which have been solubilized in a strong denaturant such as guanidine hydrochloride are renatured through preliminary sulfitolysis in the strongly denaturing solution followed by refolding, sulfonate deletion, and disulfide formation, in a weakly denaturing medium in the presence of a sulfhydryl compound containing a small percentage of its corresponding disulfide form. The disulfide form may either be supplied directly, or the sulfhydryl compound used alone in the absence of precautions to exclude air. This creates a suitably oxidizing atmosphere sufficient to insure the presence of some disulfide.

Typically, to carry out the sulfitolysis, the solubilized refractile protein in a strongly denaturing medium, such as 4–9M guanidine hydrochloride is brought to approximately 5–200 mg per ml, preferably around 15–30 mg per ml in sodium sulfite, or corresponding molar amounts of other sulfite salts, in the presence of a mild oxidizing agent sufficient to regenerate disulfide from any sulfhydryl groups which result from the reaction. Suitable oxidizing agents are, for example, molecular oxygen with catalysis by metal cations or sodium tetrathionate, preferably sodium tetrathionate. Sodium tetrathionate is added in the amount of approximately 1–20 mg/ml preferably about 10 mg per ml corresponding molar amounts of other agents may be used. The solution is then allowed to stand 4–24 hours, preferably overnight, at 15° C. to 35° C. preferably around room temperature. While suitable ranges of concentrations and temperatures, etc. have been given, the precise conditions which are most advantageous depend, of course, on the nature of the protein to be sulfitolyzed.

Furthermore, only "partial" sulfitolysis is sometimes useful. In that instance, much lesser amounts of the sulfite and oxidizer may be used. See, e.g., Example 13. The foregoing amounts are merely workable guidelines and the outer limits are defined by various parameters including the amount of protein in solution and the completeness of sulfitolysis desired.

In the above sulfitolysis reaction, the disulfide bonds are broken and a sulfonate substituted for one of the sulfide partners. It is believed that the mechanism of this reaction involves a nucleophilic attack by the sulfite ion to break the disulfide bond. In any event the resulting linkage is protein-S—$SO_3$, i.e., a protein-S-sulfonate.

The resulting protein S-sulfonate solution is then placed into a weakly denaturing solution either by dilution or by buffer exchange, e.g. by dialysis into a solution containing a weak denaturant such as urea.

It is to be noted that further purification using ion exchange chromatography or other standard protein purification techniques may be used while the protein is still in the S-sulfonated form.

The weakly denaturing medium provides a route to proper refolding, the protein no longer being trapped by incorrect disulfide linkages. If urea is used as the weakly denaturing solution, appropriate concentration ranges are 1–9M, preferably 6–8M. The pH is kept at approximately 5–9, preferably around 6–8 with suitable buffer, and optionally with added EDTA or other chelating agent. If dilution is used, appropriate concentrations are about 0.5M–2M in the original strong denaturant. To the weakly denaturing medium, a system containing a sulfhydryl compound (RSH) and its corresponding disulfide (RSSR), for example, β-mercaptoethanol, reduced glutathione, cysteamine, or cysteine and their corresponding oxidized forms, preferably glutathione in the reduced (GSH) and the oxidized (GSSG) forms, is added. The pH is adjusted to a value such that the sulfhydryl compound (RSH) is at least partially in ionized form ($RS^-$) so that nucleophilic displacement of the sulfonate is enhanced. Alternatively, the reduced form alone in the presence of air may be used, as sufficient disulfide will be generated in this environment. Typically the RSH to RSSR molar ratio is approximately between 20:1 and 5:1, preferably about 10:1 and the total glutathione or other reagent concentration in the 0.05 to 5 mM range. The mixture is incubated at about 0° C. to 37° C., depending on the protein, 4–24 hours, preferably overnight.

While the sulfhydryl compound itself would be sufficient to effect the conversion of the protein S-sulfonate to the corresponding disulfide, or at least to form disulfide linkages with the sulfhydryl compound itself, the presence of an oxidized form is required to insure that suitable disulfide linkages will remain intact. If unadulterated sulfhydryl compound is added under conditions wherein oxidation is not permitted, the protein will ultimately wind up in the sulfhydryl form, rather than as a disulfide. In order to prevent this, the oxidation potential of the surrounding buffer is maintained by supplying a small amount of the disulfide either directly or by permitting air oxidation of the reduced sulfhydryl.

The resulting solution now containing properly refolded subject protein, which presumably is secured by the correct disulfide linkages, may then optionally be stripped of denaturant by dialysis against suitable buffer solution of pH 5–9, and optionally containing small amounts of reduced glutathione or other sulfhydryl compound of the order of approximately 1 mM in concentration. If the subsequent uses of the protein are feasible in the presence of the denaturant, however, this step is unnecessary.

In foregoing procedure, the protein concentration is kept at a fairly low level, preferably less than 1 mg per ml because in some cases (though not in all), higher concentrations are detrimental to the progress of the reaction.

Further, the sulfitolysis reaction may optionally be carried out in urea or other weak denaturant as well as in the strongly denaturing solution, and it may even be advantageous to do so, particularly in instances where the denaturant concentration used to effect solution is particularly high. In such cases, the buffer exchange into weaker denaturant or dilution would be carried out before, rather than after, the sulfitolysis reaction.

In an alternative aspect of the invention designed to "refold" the heterologous protein, unfolding and refolding are made to take place in the same solution by placing the subject protein or peptide into a sulfhydryl/disulfide-containing buffer, which buffer has sufficient denaturing power that all of the intermediate conformations remain soluble in the course of the unfolding and refolding. A suitable medium is for example 1–9M urea, preferably approximately 7M urea which appears to be a weak enough denaturing agent that a close approximation to the correct conformation is permitted, and strong enough that mobility of the refolding chain, and solubility of the intermediates are possible. This embodiment may be characterized as "refolding in redox buffer." Both reduced (RSH) and oxidized (RSSR) forms of sulfhydryl compounds, for example, β-mercaptoethanol, glutathione, cysteamine, or cysteine, preferably glutathione are present in the appropriate exchange medium.

In this redox buffer refolding, the molar ratio of RSH to RSSR is approximately between 20:1 and 5:1, preferably about 10:1, and the total reagent concentration in the 0.05 to 5 mM range. The pH, again, must be sufficiently high to assure at least partial ionization of RSH, although not so high as to denature the protein. The mixture is incubated at 0° C. to 37° C., preferably about 5° C. for about 4–24 hours, preferably overnight. Here, as above, the presence of both reduced and oxidized forms of the sulfhydryl compound can be provided either directly, or through air oxidation of the sulfhydryl. Both forms need to be present in order to maintain the proper oxidizing so as to preclude complete reduction of the subject protein.

As is the case with other refolding processes of the invention, the protein may, while in solution, be subjected to standard techniques directed to purification of protein such as gel filtration or ion exchange. It is particularly preferable to employ an ion exchange technique, such as DEAE cellulose.

In a still another aspect of this invention, refolding and restoration to a native form in the context of the purification process is done by retaining the protein in a reduced form throughout whatever purification steps are conducted, and reoxidizing in the presence of air to form the appropriate disulfide linkages upon final removal of the denaturant. In this process, a reducing agent is supplied in the initial solution of refractile protein in a strong denaturant and during all of the purification steps subsequent thereto. Suitable reducing agents, are, for example, β-mercaptoethanol, dithiothreitol, and reduced glutathione, preferably β-mercaptoethanol. Upon removal of most or all of the denaturant at the end of the process, the reducing agent is not included in the reaction mixture, and sufficient air is present to reoxidize the sulfhydryl groups in the now properly folded protein to disulfide linkages so as to secure the proper native form. Employment of such a process is exemplified in Example 10 and 11 herein.

H. A Standard Multistep Procedure

An abbreviated version showing the steps required in a general multistep process for purification which forms another aspect of the invention, as well as two optional steps, selected from among those now conventionally employed, is shown as Scheme 2 below:

SCHEME 2

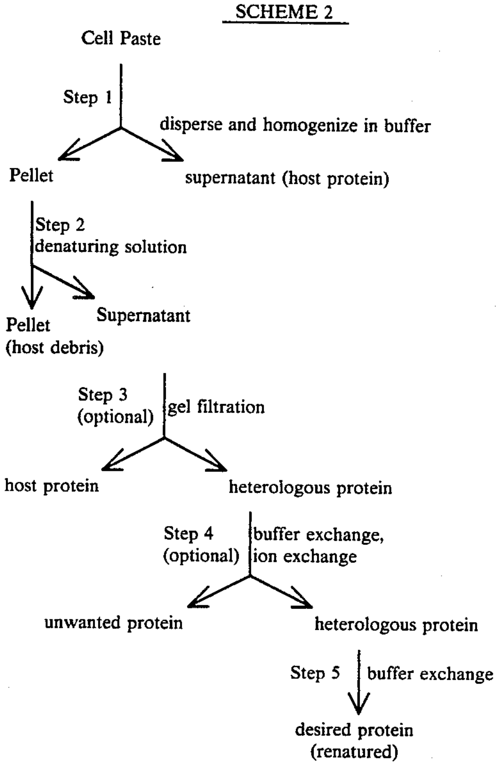

As shown in Scheme 2, the process in its basic aspect comprises dispersing a cell paste in a buffer having an ionic strength of approximately 0.05–2.0M, preferably 0.4–0.6M, to complete or maintain precipitation of the heterologous protein, and to dissolve or maintain the solubility of the majority of the host proteins. After separation from host protein, the heterologous protein is dissolved in strongly denaturing solution containing reducing agent. The process is complete upon recovery of the heterologous protein in biologically active form through buffer exchange. The gel filtration and ion exchange steps (Steps 3 and 4) are optional preferred embodiments of additional purification steps which may be appropriate in individual cases.

The cellular material used as starting material can be the whole culture or a reduced form thereof such as cell paste. Bacterial cultures are preferred, in particular, *E.*

*coli* as host cells. Currently, it is preferable to use a cell paste made subsequent to a killing step which is employed to comply with current regulations promulagated as safety precautions. (The invention is applicable for protein recovery from host cells whether or not a kill step is preliminarily employed.) In a preferred procedure, the culture broth, which is grown to approximately 30–50 OD units at 550 nm is made approximately 0.25 percent each in phenol and toluene and allowed to stand for approximately ½ hour. This is successful in killing the cells without undue denaturation of the cellular protein. Heat and acid kills are effective but less preferred; however, these and other killing methods may be used, consistent with the subsequent process of the invention. The killed materials then subjected to the procedure of the invention may be either whole broth or the centrifuged cells; however, it is preferable from a practical standpoint (of minimizing volumes) to use the centrifuged cell paste. This culture or paste may also be frozen for storage prior to the purification process purely for convenience.

In conducting the initial extraction (Step 1 of Scheme 2) the cells are dispersed thoroughly in a solution which is buffered at approximately pH 4–10, preferable from about pH 6–9, and contains ionic species at a level of approximately 0.05–2.0M ionic strength, preferably about 0.4–0.6M. Any appropriate buffer system may be used. The ionic strength is provided by any salt, including the species used for buffering, but, for reasons of economy, preferably by sodium chloride. In addition, it is desirable that the buffer contain a chelating agent, such as, for example, EDTA, and a reducing agent, for example, 2-mercaptoethanol (BME).

In carrying out the preceding step, it is highly desirable to obtain a uniform suspension; if cell paste is used, mechanical dispersal is preferred. There are dispersing machines available on the market for this purpose, and a preferable choice of Dispax (Tekmar Inc.) Model SD 45. However, if the broth culture is used, mechanical dispersal is unnecessary.

Since the heterologous precipitated (refractile) protein is usually contained within the cells, it is also necessary to homogenize the cell suspension resulting from Step 1 using a homogenizer or press of a type that will in fact destroy the integrity of the cells. A number of devices or techniques may be used, such as a French press, or a bead mill, or sonication; a Manton-Gaulin type 15M homogenizer is, however, preferred. When the cells have been dispersed and homogenized in the buffer as described, the insoluble material is separated from the soluble proteins preferably by centrifugation and the supertanant is removed. The supernatant contains primarily the host proteins and is discarded.

In a preferred procedure, the pellet is washed by redispersing the pellet in a similar buffer in order to remove still further the host materials from the insoluble proteins in the pellet. The washing is carried out in the standard fashion by treating the pellet with a fresh sample of the same buffer, redispersing and spinning down the washed pellet.

The pellet is then extracted as shown in step 2 to recover the desired heterologous proteins. The pellet is dispersed in a strongly denaturing solution by treating in a manner similar to that described in Step 1. Preferably, the solution used in this step would be 1–9 molar, most preferably 6–8 molar in a strong denaturant such as a guanidine salt, along with sufficient phosphate or other suitable buffering agents to provide a pH of approximately 4–10. preferably about 6–9, and most preferably about 7, and preferably with small amounts of chelating agent such as, for example, EDTA. It is required that a reducing agent, such as β-mercaptoethanol be present to insure conversion to free sulfhydryl groups from any disulfide linkages. Other denaturants, of course, may be used. The pellet, when dispersed, is stirred with the denaturing solution for up to 24-hours, preferably overnight.

The suspension is then spun down and the pellet, which contains undissolved and precipitated host protein and debris is discarded.

The purification to this point is sometimes sufficient that the resulting protein can be used after merely weakening the effect of denaturant through dilution or buffer exchange. If so, steps 3 and 4 can be omitted, and step 5 performed directly as described below.

In step 5, the desired protein is then recovered in biologically active form by replacing the denaturing agent with a suitable solvent medium. For some proteins, dilution to a lower concentration of the original denaturant will suffice. For others, buffer exchange into a different denaturant which is less chaotropic, such as urea is required. The final step in recovery is done in the absence of reducing agent to permit resecuring of disulfide bonds when the protein is allowed to unfold in the weaker denaturant.

However, if further purification is desired, subsequent, optional steps may be taken in the presence of reducing agent to increase purity before renaturation. A number of choices of such steps may be made. Exemplary and preferable among these are as follows:

In a first such preferred step, (step 3) the solution still containing the denaturant reducing agent and the desired protein is chromatographed by a gel filtration process for size separation. The choice of the appropriate gel pore size, because of this size dependence, depends on the nature of the protein to be purified. For the Foot and Mouth Disease (FMD) proteins the appropriate choice is, for example, Sephacryl S-300 (Pharmacia).

The gel filtration step can be carried out in the presence of the high concentration of an ionic denaturing agent which may have been used to solubilize the desired protein. However, it is clear that an ion exchange chromatography step such as that exemplified in step 4, cannot. Therefore, if still further purification is desired based on ion exchange, the denaturing solution itself, if it contains ions, e.g. guanidine or even the eluate from the gel permeation chromatography if it still contains these must first be subjected to ion removal. This can be carried out by dialysis against preferably alkaline buffer again containing reducing agent with a high concentration of a neutral denaturing agent such as, for example, approximately 8 molar urea, in order to maintain the solubilization of the heterologous protein.

When the desalting has been accomplished, the material which is in the dialysis retentate is subjected to chromatography on an appropriate ion exchange column, such as, for example, DEAE cellulose. The conditions preferably are selected so as to permit the desired protein to flow through the column in the void volume. This is advantageous, since less ion exchange resin is required if it is the trace impurities that are removed by absorption onto the resin, rather than the bulk of the protein, which at this stage of the purification procedure is the desired product.

The flow-through volume containing purified protein and (neutral) denaturant may either be used as such, in appropriate cases or freed of the denaturing agent by dialysis against a more dilute solution. It has been found that in some cases a preliminary buffer exchange into a lower concentration of urea preceding a final buffer exchange into water or buffer is required in order to prevent that precipitation of the protein. Through all steps, until the last, reducing agent must be present. Suitable reducing agents are set forth, and the rationale for their use given, hereinabove in connection with the previously described aspect of the invention.

The resulting solution is ordinarily of the order of 95–99 percent pure with respect to the desired protein. Recovery is typically of the order of at least 50 percent and up to 98 percent of the heterologous protein.

The foregoing procedure may be applied especially advantageously to hGH, pGH, bGH, bovine interferon, tPA and FMD viral coat proteins.

I. Examples

The following examples are intended to illustrate the invention but not to limit its scope.

Examples 1–8 relate to that aspect of the invention which comprises solubilization of the host cell proteins and recovery of the refractile bodies, as such, through low speed centrifugation.

Example 9 illustrates the enhancement of refractile body recovery through the use of a "kill" step.

Examples 10 and 11 relate to that aspect of the invention which comprises a multistep procedure combining a preliminary lysis and removal of bacterial proteins, with solubilization of the resulting refractile proteins and, inevitably, certain contaminants, in a strong denaturant, followed by an optional subsequent purification regime which has, as a primary step, gel filtration or high speed centrifugation and recovery of active protein. These Examples also illustrate those aspects of the invention which the use of air as the disulfide forming reagent after the protein has been allowed to refold in the presence of reducing agent, the ability of solvents which are strongly denaturing solutions to dissolve refractile bodies, and the maintenance of solubility by exchange into weaker denaturant.

Examples 12, 13, and 15 set forth the refolding of at least partially inactive protein by sulfitolysis followed by treatment with redox buffer; Example 14 sets forth the "redox buffer refolding" process.

Example 16 specifically illustrates the efficacy of solution into strongly denaturing solution followed by buffer exchange into a weaker denaturant.

All references cited in these examples are incorporated into this application by reference.

All of the examples relate to specific heterologous proteins which have been purified by the process of the invention. The details of the purification will vary, of course, with specific proteins used. Although the procedure of the invention will be similar in all cases, certain details, such as, for example, the selection of the denaturing agent in solubilizing the desired protein, the selection of appropriate sizing gels or ion exchange resins, as well as the ionic strength and pH conditions appropriate in each step, will be dependent on the nature of the protein. However, refractile proteins share enough properties in common that these minor alterations will suffice to adapt the procedure to a particular protein in question.

EXAMPLE 1

Procedure for Production and Isolation of Heterologous Proteins

A. Growth of Cells:

*E. coli* K12 cells transformed with recombinant plasmid pBR 322 carrying heterologous genes under *E. coli* trp promoter-operator control, were grown in broth containing 10 g/l yeast extracts and 5 g/l tryptone to a cell density of about $2-4\times10^8$ cells/ml. 3–5 percent of the volume of this culture was inoculated into M9 medium (J. H. Miller, *Experiments in Molecular Genetics*, p. 431, Cold Spring Harbor Laboratory, 1972) or similar mineral salts medium containing 40–120 mg/l tryptophan. The cultures were grown in a bench fermenter with sufficient agitation and aeration to achieve a growth rate of 60–90 minutes per cell division; glucose was fed to the cultures to maintain growth, but did not exceed 50 g/l during the fermentation, and the pH of the cultures was controlled at 6.8–7.2 by NaOH or $NH_4OH$. At cell density of 5–10 g dry weight/l, indole acrylic acid (IAA) or indole propionic acid (IPA) was added to the cultures to a concentration of 25–50 mg/l. Two to five hours after the addition of IAA or IPA, the *E. coli* cells became elongated and one or more refractile bodies per cell can be seen under phase contrast microscope at 1000-fold magnification.

B. Isolation of the Heterologous Protein:

The cultures were harvested by continuous centrifugation and the cell pastes were frozen at $-10°$ to $-20°$ C. (The cells may optionally be killed before harvested by addition of 0.25 percent phenol and 0.25 percent toluene added to the medium and incubating for 0.5 hrs at 37° C. (See Example 9).) Freshly harvested or frozen cell pastes were resuspended in a buffer containing 10 mM EDTA, pH 7.4 at a ratio of 1 g cell paste to 10–40 ml buffer, and the cells disrupted by sonication or homogenization under high pressure.

Under phase contrast microscope, refractile particles were seen among the cell debris. FIG. 1 shows the suspension for *E. coli* K12 strain 3110 (ATCC 27325) transformed with plasmid pUK 33trp $LE_2$, described in U.S. appln. Ser. No. 368,773, filed Apr. 15, 1982 (abandoned in favor of continuation-in-part Ser. No. 474,930, filed Mar. 14, 1983), expressing a fusion protein containing urokinase (UK). The refractile bodies appear as bright spots within the cell envelope. The suspension was subjected to centrifugation at $1,000\times g$ (Sorvall SS-34 at 3,000 rpm) for 3–10 minutes. After centrifugation, the supernatant was discarded, and the pellet was resuspended in the same buffer in 1/5 of the original volume. The suspension was examined under phase contrast microscope, and if residual intact cells or visible cell fragments were present, the above process repeated until visual examination of the resuspended pellet showed only refractile particles. FIG. 2 shows the resuspended pellet for the UK protein of FIG. 1. It appears that the preparation is mostly refractile with some cells and cell fragments included. If cells or cell fragments were present, suspension was subjected to disruption again. Isolation of refractile particles typically occurred after 3–4 cycles. The refractile particle preparation can then be stored frozen as pellet or in suspension, and is as much as 95 percent refractile protein.

To verify identity, the refractile particle preparations were subjected to SDS-PAGE, Western blot, and/or radioimmunoassay (RIA). FIG. 3 summarizes the purification results obtainable for pGH, rabies and urokinase. Rabies and pGH appear to result in single bands of protein in the pellet, urokinase is more complex because of its several allotropic forms.

EXAMPLE 2

Human Growth Hormone

Recombinant DNA *E. coli* K12 cells carrying human growth hormone gene (strain W3110/p107) as described in U.S. Pat. No. 4,342,832 were grown in fermenter and harvested, and refractile particles isolated according to the procedure described in Example 1.

The particles showed a protein band corresponding to a molecular weight standard of 22,000 daltons on 2-mercaptoethanol SDS-PAGE. A densitometer scan of the gel showed the amount of this protein was over 90 percent of the total protein in the refractile particle preparation, and the identity of this protein as human growth hormone as verified by Western blot. The yield of refractile particles was about 10–20 mg per gram of wet cell paste.

FIG. 4A shows the refractile hGH containing bodies in a suspension of the pellet from the first spin.

FIG. 4B shows the results of SDS PAGE performed on killed (with acid) and unkilled cells from this preparation. The band corresponding to hGH in pellet from killed cells is enhanced.

EXAMPLE 3

Bovine Growth Hormone (bGH)

Recombinant DNA *E. coli* K12 carrying bovine growth hormone gene (strain W3110/p BGH-1) as described in U.S. appln. Ser. No. 303,687 filed Sept. 18, 1981, was grown in fermenter and harvested, as described in Example 1. (The cells were treated with 0.25 percent phenol and 0.25 percent toluene in the fermenter before harvest.) Refractile particles were isolated and showed a single protein band in SDS-PAGE corresponding to a standard at 22,000 daltons molecular weight. A densitometer scan of the gel showed this band was over 90 percent of the total protein in the particles. After dissolving the particles in 7M guanidine and dialysis in 7M urea, the presence of bGH was verified by radioimmunoassay (RIA). The yield of refractile particles was about 20 mg per gram of wet cell paste.

EXAMPLE 4

Porcine Growth Hormone (pGH)

Recombinant DNA *E. coli* K12 carrying porcine growth hormone gene (strain W3110/pGH-exl) as described in U.S. appln. Ser. No. 439,977, filed Nov. 8, 1982, was grown in fermenter and harvested as described in Example 1. (The cells were treated with 0.25 percent phenol and 0.25 percent toluene in the fermenter before harvest.) Refractile particles were isolated showed a single protein band in SDS-PAGE corresponding to a standard at 22,000 daltons molecular weight. A densitometer scan of the gel showed this band was over 90 percent of the total protein loaded on the gel. After dissolving the particles in 7M guanidine and dialysis in 7M urea, the presence of pGH was verified by radioimmunoassay (RIA). The yield of refractile particles was about 20 mg per gram of wet cell paste. FIG. 4A shows the purity and concentration of refractile bodies containing pGH in the cell paste suspended in buffer, FIG. 4B shows this paste after sonication and FIG. 4C after low-speed spin.

EXAMPLE 5

Human Fibroblast Interferon (FIF)

Recombinant DNA *E. coli* K12 carrying human fibroblast interferon gene (strain W3110/pFIF 347) as described in Shepard, M., et.al, DNA, 1:125 (1982) was grown in fermenter and harvested, and refractile particles were isolated by the procedure described in Example 1. 2-mercaptoethanol SDS-PAGE of the resulting refractile particle preparation showed a major band corresponding to 17,000 daltons molecular weight, representing 50 percent of the total protein in the refractile particle preparation. Western blot showed the refractile protein reacted specifically to antibodies against pure human fibroblast interferon. The yield of refractile particles was about 10–20 mg per gram of wet cell paste.

EXAMPLE 6

Human Immune Interferon (IIF)

Recombinant DNA *E. coli* K12 carrying human immune interferon gene (strain W3110/pIFN-$\gamma$ trp48) as described in U.S. appln. Ser. No. 312,489 filed Oct. 19, 1981, was grown in fermenter and harvested; refractile particles were isolated by the procedure described in Example 1. 2-mercaptoethanol SDS-PAGE of the resulting refractile particle preparations showed a major band corresponding to 17,000 dalton molecular weight, representing 50 percent of the total protein in the refractile particle preparation. Western blot showed the refractile protein reacted specifically to antibodies against pure human immune interferon. The yield of refractile particles was about 10–20 mg per gram of wet cell paste.

EXAMPLE 7

Tissue Plasminogen Activator (TPA)

Recombinant DNA *E. coli* K12 carrying human tissue plasminogen activator gene, (strain 3110, pEPAtrp12) as described in U.S. appln. Ser. No. 398,003 filed July 14, 1982 (abandoned in favor of continuation-in-part Ser. No. 483,052 filed Apr. 7, 1983), was grown in a fermenter, cells harvested, and the refractile particles were isolated from cell paste according to the procedure of Example 1.

80–90 percent of the protein present in the refractile particle preparation was TPA as measured by densitometry of $\beta$-mercaptoethanol SDS-PAGE and Western blot. The yield of TPA refractile particles was about 10–20 mg per gram of wet cell paste.

EXAMPLE 8

FMD Coat Protein

Recombinant DNA *E. coli* K12 carrying various strains of foot and mouth disease virus antigen (W3110/pFMG [01], W3110/pFMB [A24], W3110/FMD [C3], W3110/FMC [A27]) as described in U.S. appln. Ser. No. 374,855 filed May 4, 1982, were grown and harvested, and the refractile particles isolated according to the procedure described in Example 1.

About 50 percent of the protein present in the refractile particle preparations were cloned FMD coat protein gene products in each case measured by densitometry of 2-mercaptoethanol SDS-PAGE and Western blot.

EXAMPLE 9

Refractile Protein Enhancement by Cell Killing Step

The amount of human growth hormone (hGH) in the cytoplasm vs the amount in refractile bodies was determined by a comparison study on killed and nonkilled cells: *E. coli* K-12 cells which were capable of expressing hGH (strain W3110/p107) (see Example 2) were grown and harvested by centrifugation as set forth in paragraph A of Example 1. Prior to centrifugation, the medium was divided and one portion was treated with 0.25 percent phenol and 0.25 percent toluene and incubated at 37° C. for four hours. The cells which were treated by killing were designated "PT" cells and those which were not killed "NPT" cells.

A. Extracts of Total Cellular Protein with SDS

Equal samples of the PT and NPT cells were subjected to identical treatment by disrupting each of the cell samples by sonication in a solution comprising 5 ml of 50 mM Tris containing 10 mM EDTA plus 250 μl of 20 percent SDS. The suspensions were vortexed for 0.5 minute, and then centrifuged. The supernatants were assayed for hGH by radio immunoassay (RIA) and by SDS PAGE. Both PT and NPT cells showed substantially identical activities in RIA, specifically $8.3\times10^6$ and $8.7\times10^6$ units per ml, respectively. Presumably, the SDS extraction procedure recovers both initially soluble and initially insoluble human growth hormone. The conforming SDS-PAGE results are shown in FIG. 6, as well as the results of SDS-PAGE performed on the samples treated as described in the next paragraph.

B. Experimental Extracts

Two further equal samples of PT and NPT cells were treated identically by extraction into 5 ml each of 50 mM Tris containing 10 mM EDTA, with vortexing for 0.5 minutes. The suspensions were then spun down at approximately $10,000\times g$ for 10 min i.e. a low speed spin (LSS) and the supernatant and pellet assayed separately. Presumably, the pellet protein will be insoluble in the absence of SDS. The NPT cells showed activity in the supernatant at a level of $4.6\times10^6$ units per ml (about ½ that of the SDS extract), but greatly diminished activity ($0.42\times10^4$ units per ml) in the pellet. The PT cells, on the other hand, showed a great reduction in hGH activity in the supernatant compared to the SDS extract, as measured by RIA $0.26\times10^4$ units per ml, and also, little activity in the pellet as solubilization of the pellet having been effected. Similar results were obtained if samples were treated correspondingly and subjected to higher speed centrifugation (HSS) i.e. $35,000\times G$ for 30 minutes.

C. Comparison of Results

FIG. 6 summarizes the results using SDS PAGE. SDS extracted cells of course, showed equivalent intensities in the band corresponding to hGH. NPT cells showed substantial amounts of the band corresponding to hGH in both the supernatant and the pellet for both high speed and low speed centrifugation separations. On the other hand, the PT cells showed a diminution both in low speed and high speed treatments of the amounts of hGH in the supernatant, but enhanced amounts in the pellet.

EXAMPLE 10

Capsid Protein of FMD Virus A Multistep Process

*E. coli* K12 harboring a gene encoding FMD virus type A24 (W3110/pFMB [A24] as described in U.S. appln. Ser. No. 374,855 filed May 4, 1982, was grown to a cell density corresponding to about 30–50 O.D. units at 550 mm; or 40 g wet cell paste per liter whole broth in M9 or similar salts medium plus tryptophan at about 40–120 mg/l and glucose at no more than about 5 percent wt/vol of medium. See *Experiments in Molecular Genetics.* (J. H. Miller, Cold Spring Harbor Laboratory, N.Y. (1972).) The culture (10 liters) was brought to 0.25 percent in each of phenol and toluene for at least ½ hour, and then centrifuged. The cell paste was frozen for convenient storage prior to protein purification. The purification as performed in this Example is outlined in Scheme 3:

SCHEME 3

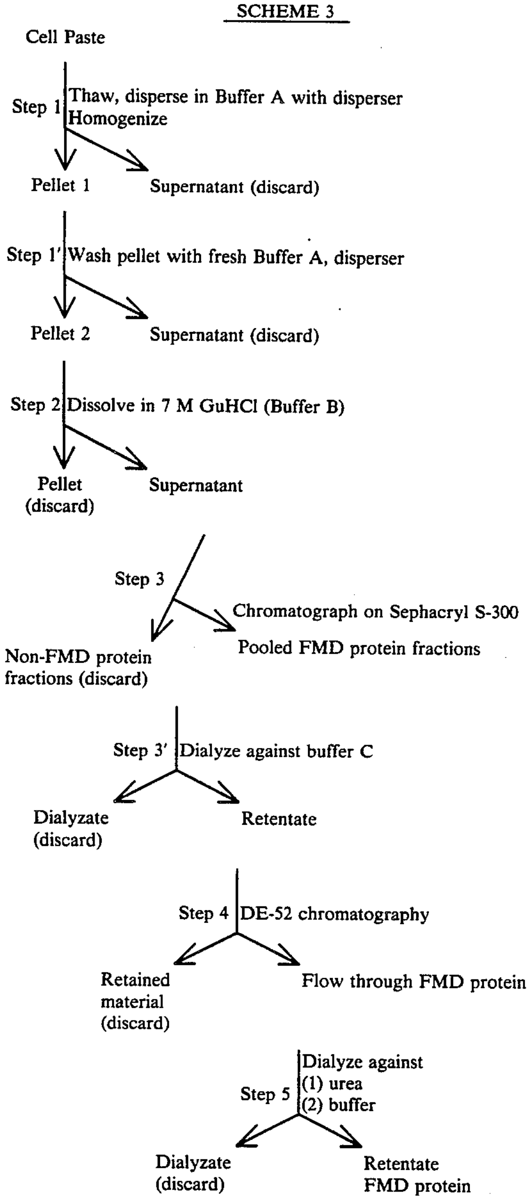

Just before use, the cell paste was thawed in a refrigerator. 500 g of the thawed paste was dispersed in 5 liters Buffer A (50 mM phosphate, 5 mM EDTA, 500 mM NaCl, 15 mM β-mercaptoethanol (BME), pH 7). A Tekmar Dispax model SD-45 with a G-450 generator (3 min. at full speed) was used to obtain a uniform suspension.

The suspension was then homogenized with a Manton-Gaulin homogenizer (Type 15M) run at 6000 psi for 2 passes, with cooling between cycles, and the homogenate centrifuged in a Beckman RC3 at 5000 rpm for 30 minutes at 4° C. SDS-PAGE showed the supernatant to contain substantially the same mixture of proteins as the uncentrifuged Manton-Gaulin homogenate, but to have a greatly diminished band corresponding to that of the FMD protein.

The pellet contained approximately one half of the initial cell paste mass. The supernatant as decanted and discarded. The pellet was washed by dispersing in fresh buffer A (2 liter/200 g pellet) using the Dispax SD-45, and the suspension centrifuged again in the RC3 at 5000 rpm for 30 minutes at 4° C. The supernatant was decanted and discarded, the pellet (137 gm) showed an enhanced band corresponding to FMD protein in SDS-PAGE, representing approximately 50 percent of the protein in the pellet.

The pellet was then extracted for FMD protein by suspending in 1 liter of Buffer B (50 mM phosphate, 1 mM EDTA, 15 mM BME, 7M guanidine hydrochloride, (GuHCl), pH 7.0) using the Dispax SD-45. The suspension was stirred overnight, and clarified by spinning in a Sorvall SS-34 rotor at 19,000 rpm for 3.0 hours at 4° C.

The pellet was discarded, and the FMD protein solution chromatographed on Sephacryl S-300 (Pharmacia). The gel was first equilibrated in Buffer B and packed in a 5×50 cm column according to manufacturer's recommendation. The void volume fractions (beginning at 270 ml) were turbid; even though the solution that was applied to the column was not. The FMD protein-containing fractions emerged at 450–650 ml and were clear. The FMD protein content was verified by dialyzing aliquots of the column fractions against 8M urea and analyzing by SDS-PAGE. (Guanidine precipitates with SDS and must be removed).

The FMD-protein containing fractions were pooled and dialyzed against four changes of a 20-fold excess of Buffer C (14 mM Tris 15 mM BME, 8M urea, pH 8.3) at 4° C. (The 8M urea substitutes for GuHCl in keeping the FMD protein in solution).

An aliquot of retentate was brought to pH 10 with NaOH and passed over a DE52 column (1.0 cm×19 cm) equilibrated with Buffer C adjusted to pH 10 with NaOH. The FMD protein was not retained by the resin, whereas the majority of the *E. coli* contaminants were adsorbed. The protein in the flowthrough volume was 96 percent FMD protein as found by SDS-PAGE and represents a yield of 30 g/kg cell paste used or about 90 percent. This material may be used as final product if the presence of urea is acceptable in the administration of active material.

In the present preparation, the urea was removed without precipitation of the FMD protein by dialysis using 4 mg/ml protein against a 250-fold volume excess of 1M urea, 14 mM Tris, 0.1 percent BME, pH 7 at 4° C., followed by dialysis of the retentate against water. A slight cloudiness formed which was removed by centrifugation. Precipitation of FMD protein in water or buffer was apparently prevented by the gradual diminution in urea concentration. The FMD protein obtained was biologically active as shown by reactivity with FMD antiserum, Western blot, and by in vivo assays in cattle wherein immune response was elicited.

EXAMPLE 11

Purification of Porcine Growth Hormone (pGH) A Multistep Process

*E. coli* K12 (W3110/pPGH-exl) (Example 4) were grown as in Example 1 to 30–50 O.D. units at 550 nm; 40 g wet cell paste per liter. The culture was brought to 0.25 percent in both phenol and toluene for ½ hour. The broth was then centrifuged and the cell paste frozen for storage.

Just before use, 384 g of the cell paste was thawed in a refrigerator, dispersed in 3.9 liters cold Buffer A (50 mM phosphate, 5 mM EDTA, 500 mM NaCl, pH 7). A Tekmar Dispax model SD-45 with a G-450 generator (3 min. at setting of 60) was used to obtain a uniform suspension, and the suspension was homogenized with a Manton-Gaulin homogenizer (Type 15M) run at 6500 psi for 2 passes, with cooling between cycles.

The homogenate (4.3 liters) was centrifuged in a Sorvall RC3 at 5000 rpm for 35 minutes at 4° C. The supernatant was decanted and shown by SDS-PAGE to contain substantially the same mixture of proteins as the homogenate before centrifuging, but with a greatly diminished band corresponding to pGH.

The supernatant was discarded and the pellet was dispersed in fresh Buffer (A (1.5 liter/150 g pellet) using the Dispax SDS-45. The suspension was centrifuged again in the RC3 at 5000 rpm for 35 minutes at 4° C. The supernatant was decanted off and discarded.

The pellet (106 g) was dissolved in 0.750 l of Buffer B (50 mM Tris, 1 mM EDTA, 100 mM BME, 7M guanidine hydrochloride, pH 8.8) using the Dispax SD-45 and then stirred overnight. The cloudy solution was clarified by spinning in a Sorvall SS-34 rotor at 19,000 rpm for 6.0 hours at 4° C., and the pellet was discarded.

690 ml of the supernatant (total volume 740 ml) was chromatographed at room temperature on a 10×85 cm Sephacryl S-300 (Pharmacia) column in two aliquots (350 ml and 345 ml). The column was equilibrated and run with 7M guanidine HCl, 50 mM Tris, 1 mM EDTA, 50 mM BME, pH 8.9. Aliquots of the column fractions were dialyzed against 8M urea 0.1 percent BME, 25 mM Tris, pH 7, and analyzed by SDS-PAGE, to determine the presence of pGH.

The pGH-containing fractions were pooled and dialyzed against four changes of an approximately 20-fold excess of 15 mM Tris HCl, 50 mM BME, 7M urea, pH 9.0 at 4° C. The retentate (3900 ml) was brought to pH 7.0 with HCl and passed over a DE52 column (10 cm×11.5 cm) equilibrated with 15 mM Tris, 7.5M urea, 50 mM BME, pH 7.0 at room temperature. The column was flushed with 1 column volume equilibrating buffer to wash out entrained pGH.

The DE52 pool (4000 ml) was titrated to pH 10 with NaOH, and dialyzed in Spectrapor 1 against three 100-liter changes of 25 mM Tris, 1 percent mannitol, pH 10 at 4° C. The retentate was pooled, and diluted to 10.4 liters with dialysate, sterile filtered, and lyophilized. Ten g of biologically active protein (by Western blot) of 98 percent purity in pGH was obtained.

EXAMPLE 12

Refolding of Prorennin using Sulfitolysis 432 grams of cell paste from *E. coli* K-12 (strain W3110/pRIAX, which carries the gene encoding for prorennin as described in copending application docket number 100/130) were suspended in 3 liters of buffer comprising 50 mM Tris HCl, 5 mM EDTA, pH 7.5. The suspension was subjected to cellular disruption by a Manton Gaulin press at 6,000 psi for four passes. The disrupted suspension was then centrifuged for 30 minutes at 4,000×g and the supernatant removed and discarded. The pellet was resuspended in 2 liters of the same buffer as was used in the original suspension and again centrifuged for 30 minutes at 4,000×g. The supernatant was again discarded and the pellet dissolved in 6M guanidine hydrochloride containing 50 mM Tris at pH 8. The solubilized refractile protein was then sulfonated by bringing the guanidine solution to 20 mg/ml in sodium sulfite and 10 mg/ml in sodium tetrathionate by adding an aliquot of a clarified stock solution freshly prepared of these components. The sulfonation was allowed to proceed for four hours at room temperature.

The solution was then diafiltered into 5M urea containing 50 mM Tris HCl, pH 7.5 for five hours. The diafiltered solution was then placed on a 10×35 cm column of DE52 which had been washed with the same "binding" buffer solution (5M urea, 50 mM Tris HCl, pH 7.5). The solution was loaded at 750 ml per hour and washed overnight with the binding buffer.

The DE52 column was then eluted using a 0 to 0.15M NaCl gradient with a flow rate of 1 liter per hour over a 16 hour period. The majority of the protein eluted at approximately 0.070M NaCl. The prorennin containing fractions were again diafiltered against 5M urea, 50 mM Tris HCl pH 8.5 and the solution brought to 1 mM in GSH and 0.1 mM in GSSG and allowed to incubate at room temperature overnight. An additional diafiltration to remove urea was conducted against 50 mM Tris, pH 8.0 containing 0.1 mM GSH. The resulting solution, free of denaturant, contained 5.5 grams of protein, or approximately 1 percent yield overall. The protein showed biological activity by reaction against prorennin antiserum and by activity (after autocatalytic activation) in a standard milk clotting assay.

EXAMPLE 13

Preparation of Active Urokinase Through Partial Sulfitolysis

Urokinase containing refractile bodies were isolated from *E. coli* K12 (strain W3110/pUK 33trpLE$_L$) as described in U.S. appln. Ser. No. 368,773 filed Apr. 15, 1982 (abandoned in favor of continuation-in-part Ser. No. 474,930 filed Mar. 14, 1983) by the procedure set forth in Example 1. The refractile bodies were dissolved in 5M guanidine HCl, containing 50 mM Tris, pH 8.0. The solution was brought to 0.2 mg per ml in sodium sulfite and 0.1 mg per ml sodium tetrathionate, and incubated overnight at room temperature.

The solution was then diluted to a level of 1.5M guanidine HCl with pH 9.0, 50 mM Tris buffer, and brought to 10 mM GSH: 1 mM GSSG. The diluted guanidine solution containing the dissolved protein was then again incubated overnight at room temperature and dialyzed into aqueous solution. While the refractile bodies showed activity in a standard bioassay for urokinase of 0.25 PU/mg, the urokinase resulting from the procedure herein set forth gave an activity of 150 PU/mg.

EXAMPLE 14

Reactivation of Urokinase by Redox Buffer Refolding

Refractile bodies prepared as set forth in Example 13 were dissolved in 5M guanidine hydrochloride in 50 mM Tris, pH 8.0, and then the solution dialyzed into 2M urea, 50 Tris hydrochloride pH 7. The solution was then brought to 10 mM GSH: 1 mM GSSG and incubated overnight at room temperature. The resulting solution containing refolded protein was then dialyzed into aqueous medium. The resulting solution contained urokinase which showed 30 PU/mg activity.

EXAMPLE 15

Refolding of Sarc Protein

Sarc, a protein originally isolated from sarcoma tumors was obtained by applying the procedures of Example 1 to transformed cells prepared according to the procedure set forth in McGrath, J. P. and Levinson, A. D., *Nature,* 295: 423 (1982). To 3 mg of this protein which was insoluble under native buffer conditions, was added 3 ml 7M guanidine, 300 μl 1M Tris, pH 8, 20 μl 0.5M EDTA and 400 μl of a solution containing 200 mg per ml sodium sulfite and 100 mg per ml sodium tetrathionate. The solution was let stand at room temperature overnight and remained a cloudy suspension.

The suspension was dialyzed against 7M urea containing 5 mM Tris, pH 8. To half of this solution was added 300 μl 0.1M glycine, pH 9.5 and 90 μl 10 mM β-mercaptoethanol; and the solution allowed to stand overnight. After dialysis against 50 mM Tris, pH 8.5, the same protein was soluble and was capable when injected into mice of inducing antibodies precipitable against authentic sarc protein.

EXAMPLE 16

Solution in Guanidine and Extraction into Urea

*E. coli* K/2 (W3110/pFMB [A24]) (Example 8) was grown as described in Paragraph A of Example 1 and harvested by centrifugation. The cell paste (281 g wet weight) was suspended in 10 volumes phosphate extraction buffer (PEB: 50 mM $NaH_2PO_4$, 5 mM EDTA, 0.5M NaCl, 0.1 percent BME, pH 7.0) with an ultratorex. The résulting suspension was passed through a prechilled Manton Gaulin twice at 600 psi and 1 liter/minute. After centrifugation at 5000 rpm (½ hour) in RC5B centrifuge the pellet was resuspended in 10 volumes PEB with an ultratorex (10 min.) The suspension was centrifuged at 5000 rpm in RC5B centrifuge for ½ hour and the resulting pellet taken up in 20 volumes Urea-Tris buffer (UTB: 8M urea (freshly prepared and deionized), 0.14M Tris, 0.1 percent BME, pH 8.3) and heated for ½ hour in a boiling water bath. After cooling to room temperature, 4 volumes of acetone were added and the solution was stirred at −6° C. for 1½ hours. The suspension was then centrifuged at 5000 rpm in the RC3B and the resulting pellet taken up in 10 volumes PEB. After heating the suspension for ½ hour on a boiling water bath the material was recentrifuged in RC5B at 5000 rpm and the resulting pellet resuspended for 48 hours in 2.2 liters 7M GuHCl, 0.1 percent BME.

The sample was then dialyzed versus 3 changes of UTB at pH 8.0 and then chromatographed on a DE-52 cellulose column (5×8 cm) equilibrated with UTB, pH 8.0. The column wash was collected as two fractions, a clear and turbid fraction. The clear fraction (>90 percent VP3) was concentrated to −1.3 mg/ml and tested for biological activity.

A control batch of antigen was prepared using *E. coli* K12 (W3110/pFMB [A24]) grown, harvested, and treated as above, but wherein UTB was substituted for GuHCl in taking up the pellet.

Samples were tested by injecting into guinea pigs and obtaining the antiserum after 28 days. The antiserum was then tested for antibody titer by ability to protect suckling mice from FMD virus. The results are expressed as the negative log of the dilution of antiserum capable of conferring immunity on 50 percent of the mice ($-\log PD_{50}$).

Antisera from injection of 100 $\mu g$ protein of the above preparation had $-\log PD_{50}$ values of 3.2–3.4, while antisera from injections of 100 $\mu g$ protein of extracts made from the controls had log $PD_{50}$ values less than 0.3.

We claim:

1. A process for isolating, purifying and reactivating heterologous proteins which are precipitated as refractile bodies in host cells, which process comprises:
   (a) treating the host cell culture with a buffered solution of ionic strength suitable to solubilize protein but in which refractile heterologous protein is substantially insoluble and disrupting the cells, to form a supernatant and an insoluble fraction;
   (b) treating the insoluble fraction from step (a) with a strongly denaturing solution containing a reducing agent to solubilize the refractile heterologous protein;
   (c) replacing the strongly denaturing solution with a weakly denaturing solution containing a reducing agent; and
   (d) reactivating the solubilized protein by removing most or all of the weak denaturant and reducing agent in the presence of air, to produce active heterologous protein.

2. The process of claim 1 wherein there is employed in step (a) a cell paste or a frozen and thawed cell paste.

3. The process of claim 1 wherein the host cell culture is a culture of *E. coli.*

4. The process of claim 1 wherein the heterologous protein is selected from the group consisting of hGH, pGH, bGH, bovine interferon, tPA, and FMD viral coat proteins.

5. The process of claim 1 which includes the prior step of killing the host culture with non-polar solvent or detergent.

6. The process of claim 1 which includes the step of subjecting the solution resulting from step (b) to gel permeation chromatography in the presence of reducing agent.

7. The process of claim 6 which includes the step of subjecting those fractions resulting from gel permeation chromatography which contain heterologous protein to salt removal, and treating the desalted solution with an ion exchange resin at a pH at which the heterologous protein does not adsorb to the ion exchange resin all in the presence of reducing agent.

8. The process of claim 1 wherein the buffered solution in (a) is about 0.05–2.0M in ionic strength and buffered at about pH 4–10.

9. The process of claim 8 wherein the buffered solution in (a) is about 0.4–0.6M in ionic strength and buffered at about pH 6–9.

10. The process of claim 1 wherein the strongly denaturing solution is guanidine HCl in a concentration of about 1–9M.

11. The process of claim 10 wherein the concentration of guanidine HCl is about 6–8M.

12. The process of claim 1 wherein the buffered solution of Step (a) contains a reducing agent.

13. The process of claim 1 or 13 wherein there is employed $\beta$-mercaptoethanol as the reducing agent.

14. The process of claim 1 which includes the additional step of separating host culture into broth and cell paste before carrying out Step (a) on the paste.

15. The process of claim 1 which includes additional purification steps conducted in the presence of reducing agent.

16. Protein reactivated by the process of claim 1.

* * * * *

UNITED STATES PATENT AND TRADEMARK OFFICE
CERTIFICATE OF CORRECTION

PATENT NO. : 4,620,948

DATED : November 4, 1986

INVENTOR(S) : Stuart E. Builder et al

It is certified that error appears in the above-identified patent and that said Letters Patent is hereby corrected as shown below:

Column 31, line 16, after "host cells, insert -- said proteins not subjected to CNBr treatment,".

Column 31, line 19, after "which" insert -- said --.

Signed and Sealed this

Tenth Day of May, 1988

*Attest:*

DONALD J. QUIGG

*Attesting Officer*

*Commissioner of Patents and Trademarks*